United States Patent [19]

Bodor et al.

[11] 4,049,818
[45] Sept. 20, 1977

[54] 3-CHLORO-1,3-OXAZINES OR OXAZOLIDINES AS ANTIBACTERIAL AGENTS

[75] Inventors: Nicolae S. Bodor; James J. Kaminski, both of Lawrence, Kans.

[73] Assignee: INTERx Research Corporation, Lawrence, Kans.

[21] Appl. No.: 654,870

[22] Filed: Feb. 3, 1976

Related U.S. Application Data

[62] Division of Ser. No. 566,747, April 10, 1975, Pat. No. 3,954,985, which is a division of Ser. No. 456,744, April 1, 1974, Pat. No. 3,897,425.

[51] Int. Cl.$^2$ .............................................. A01N 9/22
[52] U.S. Cl. .................................. 424/272; 424/248; 424/267; 424/248.4; 424/248.56; 424/248.55; 424/248.57
[58] Field of Search ..................... 424/267, 272, 248

[56] References Cited

U.S. PATENT DOCUMENTS

| | | | |
|---|---|---|---|
| 3,881,908 | 5/1975 | Dorschner et al. | 260/307 FA |
| 3,954,985 | 5/1976 | Bodor et al. | 424/248 |

*Primary Examiner*—V. D. Turner
*Attorney, Agent, or Firm*—Charles N. Blitzer

[57] ABSTRACT

There is provided, novel 3-chloro-tetrahydro-1,3-oxazine or oxazolidine compounds, exhibiting antibacterial activity and being of low chlorine potential of the formula:

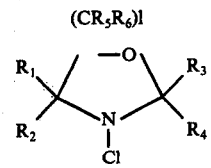

wherein each of $R_1$ and $R_2$, which may be the same or different, represent an alkyl group of from 1 to 20 carbon atoms ($C_1$-$C_5$ being preferred); wherein each of $R_5$ and $R_6$, which may be the same or different, represent a hydrogen atom or an alkyl group of from 1 to 20 carbon atoms ($C_1$-$C_5$ being preferred); wherein l represents an integer of 1 or 2 and wherein each of $R_3$ and $R_4$, which may be the same or different, represent an alkyl group of from 1 to 20 carbon atoms ($C_1$-$C_5$ being preferred) a —$(CH_2)_n$X group, wherein $n$ represents an integer of from 1 to 20 and wherein X represents a dimethylamino group, a diethylamino group, a trimethylammonium group, a triethylammonium group, a dimethylammonium group, a diethylammonium group, a —$COOR_7$ group, a —$OOCR_8$ group, and a —$OR_9$ group, wherein each of $R_7$ through $R_9$, respectively, represent an alkyl group of from 1 to 5 carbon atoms or a benzyl group. In addition, $R_3$ and $R_4$ can also represent a

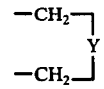

group, wherein Y represents a —$(CH_2)_n$—W—$(CH_2)_m$— group or a >CH—Z group, wherein W represents a —O— atom, a —$CH_2$— group, a >$NCH_3$— group, a >$NHCH_3^+$ group, a >$NC_2H_5$ group, a >$NHC_2H_5^+$ group, a >$N(CH_3)_2^+$ group, or a >$N(C_2H_5)_2^+$ group, wherein $n$ is the same or different from $m$ and wherein each of $n$ and $m$ represent an integer of from 0 to 2; and wherein Z is defined in accordance with X above.

5 Claims, No Drawings

3-CHLORO-1,3-OXAZINES OR OXAZOLIDINES AS ANTIBACTERIAL AGENTS

CROSS-REFERENCE TO RELATED APPLICATONS

This application is a divisional application of our earlier co-pending application, Ser. No. 566,747, filed Apr. 10, 1975 now U.S. Pat. No. 3,954,985, which in turn was a divisional application of still earlier co-pending application, Ser. No. 456,744, filed Apr. 1, 1974, now U.S. Pat. No. 3,897,425.

BACKGROUND OF THE INVENTION

1. Field of the Invention

The present invention is directed to novel antibacterial low chlorine potential compounds and more specifically, the present invention is directed to a totally new class of such compounds, termed 3-chloro-tetrahydro-1,3-oxazines or oxazolidines as described hereinafter.

2. Description of the Prior Art

It is known in the art that certain N-chloro-2-oxazolidinones possess antibacterial activity. However, a review of the literature concerning such compounds will readily reveal that these compounds are higher chlorine potential compounds and as a result thereof, while such compounds can exhibit a sufficient antibacterial activity, their higher chlorine potential imparts to these compounds, a "bleach" capability. That is, due to their high chlorine potential, the N-chloro-2-oxazolidinones, while capable of controlling bacterial growth, will also tend to be more corrosive. Consequently, for the most part, these compounds have been employed as bleaching agents. See, U.S. Pat. No. 3,591,601.

SUMMARY OF THE INVENTION

In view of the foregoing, it is readily apparent that there is a great need to develop suitable antibacterial agents of low chlorine potential, which exhibit sufficient antibacterial activity and yet, are less corrosive.

Therefore, it is one object of the present invention to develop antibacterial agents of low chlorine potential, which exhibit sufficient antibacterial activity.

It is a second object of the present invention to develop antibacterial agents which in addition to exhibiting sufficient antibacterial activity and of being of low chlorine potential, also fail to be relatively corrosive.

Finally, it is a third object of the present invention to develop antibacterial agents which meet the above criteria and yet, are non-persistant. That is, compounds which, in aqueous media, exhibit sufficient antibacterial activity over a short time span, afterwhich, decomposition of the compound occurs.

Accordingly, with the foregoing in mind, the present invention is directed to a novel class of low chlorine potential compounds, which exhibit antibacterial activity and are deemed non-persistant, which compounds have the following formula:

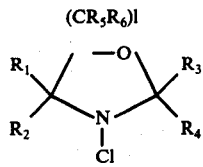

wherein each of $R_1$ and $R_2$, which may be the same or different, represent an alkyl group of from 1 to 20 carbon atoms ($C_1$–$C_5$ being preferred); wherein each of $R_5$ and $R_6$, which may be the same or different, represent a hydrogen atom or an alkyl group of from 1 to 20 carbon atoms ($C_1$–$C_5$ being preferred); wherein $l$ represents integer of 1 or 2 and wherein each of $R_3$ and $R_4$, which may be the same or different, represent an alkyl group of from 1 to 20 carbon atoms ($C_1$–$C_5$ being preferred), a —$(CH_2)_n$X group, wherein $n$ represents an integer of from 1 to 20 and wherein X represents a dimethylamino group, a diethylamino group, a trimethylammonium group, a triethylammonium group, a dimethylammonium group, a diethylammonium group, a —$COOR_7$ group, a —$OOCR_8$ group, a —$OR_9$ group, wherein each of $R_7$ through $R_9$, respectively, represent an alkyl group of from 1 to 5 carbon atoms or a benzyl group. In addition, $R_3$ and $R_4$ can also represent a

group, wherein Y represents a —$(CH_2)_n$—W—$(CH_2)_m$— group or a >CH-Z group, wherein W represents an —O— atom, a —$CH_2$— group, a >$NCH_3$— group, a >$NHCH_3^+$ group, a >$NC_2H_5$ group, a >$NHC_2H_5^+$ group, a >$N(CH_3)_2^+$ group, or a >$N(C_2H_5)_2^+$ group, wherein $n$ is the same or different from $m$ and wherein each of $n$ and $m$ represent an integer of from 0 to 2; and wherein Z is defined in accordance with X above.

In the case where $R_5$ and $R_6$ may represent an alkyl group of from 1 to 20 carbon atoms or a hydrogen atom, the hydrogen atom form is preferred. This is true even when $R_5$ and $R_6$ represent a carbon atom range of from 1 to 5.

Where feasible, applicants prefer to use the proton salt (HX salt), wherein X represents a pharmaceutically acceptable anion derived from a pharmaceutically acceptable acid addition salt of the compound, though use of the free base is quite acceptable. The proton salts can easily be prepared by simply reacting the free base compound with a pharmaceutically acceptable acid, such as hydrochloric acid, hydrobromic acid, methanesulfonic acid, and the like.

At this point, it should be emphasized that the term "antibacterial" as employed in this application also includes "antifungal" activity as well.

The compounds of the present inventon are readily prepared by the synthesis procedure outlined below, wherein $R_1$, $R_2$, $R_3$, $R_4$, $R_5$, $R_6$ and $l$, are defined as above.

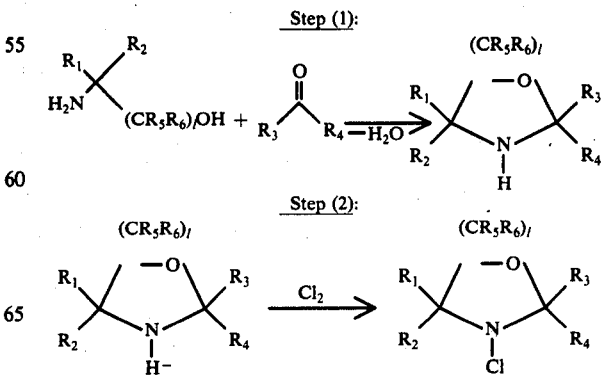

The above reaction scheme is carried out under standard temperature and pressure. With respect to step (1), the solvent employed is one which is capable of removing water from the first reaction step as it is formed. Without limitation, illustrative solvents capable of achieving this function are benzene, toluene, or xylene. As an alternative embodiment, a desiccant, such as magnesium sulfate or a molecular sieve can be employed to remove water formed during the reaction.

As for step (2), any conventional chlorinating agent can be employed and illustrative of such agents, suitable for applicants' purpose is NaOCl, Ca(OCl)$_2$, t-BuOCl, N-chlorosuccinimide and chlorine. Naturally, the aforementioned chlorinating agents are only illustrative of the wide variety of conventional chlorinating agents suitable for applicants' purpose and it is believed that this is understood by the skilled artisan concerned with the subject matter of this invention.

A better understanding of the present invention will be gained from a review of the following examples, which are simply illustrative and non-limitative thereof.

EXAMPLE I

Preparation of 3-chloro-2,2,4,4-tetramethyl-tetrahydro-1,3-oxazolidine

Firstly, the precursor compound (2,2,4,4-tetramethyl-1,3-oxazolidine was prepared. To 237 g (3.0 mole) of 2-amino-2-methyl-1-propanol, there was added approximately 750 ml of dry benzene containing 174 g (3.0 mole) of acetone.

A few crystals of para-toluenesulfonic acid were added to the reaction mixture and the solution was stirred under a Dean-Stark water separator at relux temperature. When the theoretical amount of water was collected, the reaction mixture was distilled at atmospheric pressure. The 2,2,4,4-tetramethyl-tetrahydro-1,3-oxazolidine was collected as a clear, colorless distillate, bp 128°–130° C, 220 g (1.7 mole), 57% yield.

Analysis Calculated for: $C_7H_{15}NO$: C, 65.07; H, 11.70; and N, 10.84. Found: C, 65.34; H, 11.80; and N, 11.00.

Next, the final compound (3-chloro-2,2,4,4-tetramethyl-tetrahydro-1,3-oxazolidine) was prepared from the precursor material. To 175 ml of 0.65 M sodium hypochlorite (0.11 mole) at 0° C, there was added dropwise with stirring, the precursor compound obtained earlier, while the reaction mixture was maintained between a pH of from 4 to 6 through the use of 1M HCl.

After 30 minutes at 0° C, the reaction mixture was extracted with dichloromethane and the extracts were combined and dried over anhydrous sodium sulfate. Following filtration, the dichloromethane was removed under reduced pressure and the 3-chloro-2,2,4,4-tetramethyl-tetrahydro-1,3-oxazolidine was isolated as a pale yellow liquid, bp 65°–67° C (12 mm), 10.1 g (0.062 mole), a 56% yield.

Analysis Calculated for: $C_7H_{14}ClNO$: C, 51.37; H, 8.62; N, 8.56 and Cl, 21.7. Found: C, 51.36; H, 8.77; and Cl, 19.2.

Once the final compound was prepared, it was subjected to antibacterial and stability studies as described in Tables 1 and 2, set forth on the following pages.

TABLE 1

| COMPOUND | CONDITIONS pH | : DILUENT | CONCENTRATION DATA COMPOUND ; POSITIVE Cl | GERMICIDAL ACTIVITY TIME (MIN) BACTERIA | | | | | |
|---|---|---|---|---|---|---|---|---|---|
| | | | | 12228 | 10536 | 10031 | 9027 | 6538 | 4617 |
| [structure: 2,2,4,4-tetramethyl-3-chloro-1,3-oxazolidine] | 0.1M NaOAc pH 4.6 | : H$_2$O | 8.26 × 10$^{-3}$M ; 289 ppm 1355 ppm | 0.5 | 0.5 | 0.5 | 0.5 | 0.5 | 0.5 |
| | 0.1M NaOAc pH 4.6 | : Serum | 8.26 × 10$^{-3}$M ; 289 ppm 1355 ppm | >10 | 3 | >10 | 4 | >10 | 6 |
| [structure: 2,2,4,4-tetramethyl-3-chloro-1,3-oxazolidine] | 0.1M NaH$_2$PO$_4$ pH 7.00 | : H$_2$O | 8.92 × 10$^{-3}$M ; 312 ppm 1463 ppm | 1 | 0.5 | 0.5 | 1 | 3 | 1 |
| | 0.1M NaH$_2$PO$_4$ pH 7.00 | : Serum | 8.92 × 10$^{-3}$M ; 312 ppm 1463 ppm | 6 | 3 | 5 | 7 | >10 | >10 |
| [structure: 2,2,4,4-tetramethyl-3-chloro-1,3-oxazolidine] | 0.1M Na$_2$B$_4$O$_7$ pH 8.8 | : H$_2$O | 8.13 × 10$^{-3}$M ; 285 ppm 1333 ppm | >5 | 2 | 4 | 2 | >5 | 3 |
| | 0.1M Na$_2$B$_4$O$_7$ pH 8.8 | : Serum | 8.13 × 10$^{-3}$M ; 285 ppm 1333 pp | >10 | 4 | 9 | 4 | >10 | 8 |

TABLE 2

STABILITY ANALYSIS OF 3-CHLORO-2,2,4,4-TETRAMETHYL-1 TETRAHYDRO-1,3-OXAZOLIDINE

[structure: 2,2,4,4-tetramethyl-3-chloro-1,3-oxazolidine] ⟶ Conditions

| CONDITIONS | | | | |
|---|---|---|---|---|
| Buffer | pH | T (° C) | Initial concentration of 3 | Half-life (hr.) |
| 0.1 M NaOAc | pH 4.6 | 40 | 1.88 × 10$^{-3}$ M | 2.2 |
| | | | 2.59 × 10$^{-3}$ M | 2.2 |
| | | | 5.47 × 10$^{-3}$ M | 2.6 |
| 0.1 M NaH$_2$PO$_4$ | pH 7.0 | 40 | 1.68 × 10$^{-3}$ M | ~70 |
| | | | 3.05 × 10$^{-3}$ M | ~54 |
| | | | 6.70 × 10$^{-3}$ M | ~54 |
| 0.1 M Na$_2$B$_4$O$_7$ | pH 9.3 | 40 | 1.52 × 10$^{-3}$ M | ~5.0 |
| | | | 2.49 × 10$^{-3}$ M | ~4.6 |
| | | | 5.98 × 10$^{-3}$ M | ~3.3 |

TABLE 2-continued
STABILITY ANALYSIS OF 3-CHLORO-2,2,4,4-TETRAMETHYL-1 TETRAHYDRO-1,3-OXAZOLIDINE

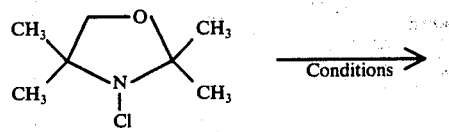

| CONDITIONS | | | | |
|---|---|---|---|---|
| Buffer | pH | T (° C) | Initial concentration of 3 | Half-life (hr.) |
| H₂O | | | 6.23 × 10⁻³ M | ~58 |

EXAMPLE II

Preparation of 3-chloro-2,2-[spiro-1'-methyl-4'-piperidinyl]-4,4-dimethyl-1,3-oxazolidine and its HX salts Firstly, the precursor compound, 2,2-[spiro-1'-methyl-4'-piperidinyl]-4,4-dimethyl-1,3-oxazolidine was prepared. To 44.5 g (0.5 mole) of 2-amino-2-methyl-1-propanol, there was added approximately 400 ml of dry benzene containing 56.5 g (0.5 mole) of 1-methyl-4-piperidone. The solution was stirred under a Dean-Stark water separator at reflux temperature.

When the theoretical amount of water was collected, the benzene was removed under reduced pressure to yield a brown oil. The precursor compound was collected as a clear, colorless distillate, bp 63°-65° C (1.2 mm), 58.9 g (0.32 mole), 64% yield.

Next, the final compound 3-chloro-2,2-[spiro-1'-methyl-4'- piperidinyl]-4,4-dimethyl-1,3-oxazolidine was prepared from the precursor material in the manner described. To 50 ml of 0.65 M sodium hypochlorite (0.03 mole) at 0° C, there was added with stirring 5.52 g (0.03 mole) of the precursor compound obtained earlier.

After 30 minutes at 0° C, the pale yellow solid was isolated by filtration, washed thoroughly with cold water and then dried in vacuo over calcium sulfate to give 3-chloro-2,2-[spiro-1'-methyl-4'-piperidinyl]-4,4-dimethyl-1,3-oxazolidine, mp 46°-48° C, sublimation at 35° C (0.5 mm); UV (H₂O) λ max 265 nm, $\epsilon$=270 $M^{-1}cm^{-1}$.

Analysis Calculated for: $C_{10}H_{19}ClN_2O$: C, 54.91; H, 8.76; N, 12.81; and Cl, 16.2. Found: C, 54.77; H, 8.90; N, 12.85; and Cl, 15.1.

PREPARATION OF THE HX SALTS

The methanesulfonate salt of the above-isolated compound was prepared by simply reacting the free base with an ethereal solution of methanesulfonic acid, mp 124°-125° C (dec).

Analysis Calculated for: $C_{11}H_{23}ClN_2O_4S$: C, 41.96; H, 7.36; N, 8.90; and Cl, 11.3. Found: C, 41.27; H, 7.41; N, 8.49; and Cl, 10.6

In similar fashion, the hydrochloride salt of the above-isolated compound was prepared as follows. To an ethereal solution containing 1.1 g (0.005 mole), at 0° C, there was added dropwise with stirring, 2 ml of 2.26 M HCl/Et₂O, diluted to approximately 25 ml using anhydrous ether, (0.0045 mole). The suspension was maintained at 0° C for 30 minutes and the white solid which formed was isolated by filtration and thoroughly washed with anhydrous ether under an atmosphere of nitrogen. The solid isolated was dried in vacuo over calcium sulfate to give the corresponding hydrochloride salt, mp 120°-121° C (dec.), 1.18 g (0.0046 mole), 93% yield.

Analysis Calculated for: $C_{10}H_{20}Cl_2N_2O$: C, 47.06; H, 7.90; N, 10.98; Cl, 13.9. Found: C, 44.39; H, 7.56; N, 9.91; and Cl, 13.1.

Tables 3 and 4, set forth on the following pages, illustrate the antibacterial activity and stability values obtained from the free-base and the methanesulfonate salt prepared by the procedure described in Example II. Tables 5 and 6, set forth on the following pages, illustrate the stability values determined for the hydrochloride and methanesulfonate salts of the free-base compound prepared by the procedure of Example II.

TABLE 3
ANTIBACTERIAL ACTIVITY OF 3-CHLORO-2,2-[-METHYL-4'-PIPERIDINYL]-4,4-DIMETHYL-1,3-OXAZOLIDINE

| Compound | Conditions Buffer/pH | Diluent | Concentration Data Compound | Positive Cl | 12228 | 10536 | 10031 | 9025 | 6538 | 4617 | 6501 |
|---|---|---|---|---|---|---|---|---|---|---|---|
| (structure) | 0.1 M NaOc pH 4.6 0.1 M NaOAc pH 4.6 | H₂O Serum | 6.52 × 10⁻³M 1428 ppm 5.69 × 10⁻³M 1246 ppm | 231 ppm 202 ppm | 1 >10 | 0.5 2 | 0.5 7 | 0.5 >10 | 5 >10 | — — | 0.5 3 |
| (structure) | 0.5 M NaOAc pH 4.6 0.5 M NaOAc pH 4.6 | H₂O Serum | 21.00 × 10⁻³M 4578 ppm 20.50 × 10⁻³M 4469 ppm | 745 ppm 727 ppm | 0.5 2 | 0.5 0.5 | 0.5 0.5 | 0.5 1 | 0.5 3 | 0.5 1 | 0.5 0.5 |
| (structure) ⁻OSO₂CH₃ | 0.5 M NaOAc pH 4.6 0.5 M NaOAc pH 4.6 | H₂O Serum | 17.0 × 10⁻³ 5355 ppm 17.0 × 10⁻³ 5355 ppm | 603 ppm 603 ppm | 0.5 2 | 0.5 0.5 | 0.5 1 | 0.5 1 | 1 6 | 0.5 1 | 0.5 1 |

TABLE 4
ANTIBACTERIAL ACTIVITY OF 3-CHLORO-2,2-[SPIRO-1'-METHYL-4'-PIPERIDINYL]-4,4-DIMETHYL-1,3-OXAZOLIDINE

| Compound | Conditions Buffer/pH | Diluent | Concentration Data Compound | Positive Cl | Antibacterial Activity, Time (min.) | | | | | | |
|---|---|---|---|---|---|---|---|---|---|---|---|
| | | | | | 12228 | 10536 | 10031 | 9027 | 6538 | 461 | 6501 |
| [structure: 3-chloro-2,2-[spiro-1'-methyl-4'-piperidinyl]-4,4-dimethyl-1,3-oxazolidine] | 0.5 M NaH$_2$PO$_4$ pH 7.0 | H$_2$O | 20.75 × 10$^{-3}$M 4525 ppm | 736 ppm | 1 | 0.5 | 1 | 1 | 1 | 0.5 | 1 |
| | 0.5 M NaH$_2$PO$_4$ pH 7.0 | Serum | 19.88 × 10$^{-3}$M 4334 ppm | 705 ppm | 5 | 7 | 8 | 10 | >10 | 5 | 7 |
| [structure with -OSO$_2$CH$_3$] | 0.5 M NaH$_2$PO$_4$ pH 7.0 | H$_2$O | 19.75 × 10$^{-3}$M 6221 ppm | 700 ppm | 4 | 1 | 1 | 1 | 4 | 1 | 1 |
| | 0.5 M NaH$_2$PO$_4$ pH 7.0 | | 19.13 × 10$^{-3}$M 6026 ppm | 678 ppm | >10 | 4 | >10 | >10 | >10 | >10 | >10 |

TABLE 5
STABILITY OF 3-CHLORO-2,2-[SPIRO-1'-METHYL-4'-PIPERIDINAL 4,4-DIMENTHYL-1,3-OXAZOLIDINE HYDROCHLORIDE IN THE NEAT STATE AT 40° C

| TIME(days) | Wt. (mg)$^a$ | V$_T$(ml)$^b$ | %Cl$^c$ |
|---|---|---|---|
| 0 | 29.11 | 22.60 | 13.7 |
|  | 48.50 | 35.95 | 13.1 |
| 1 | 35.15 | 24.50 | 12.3 |
|  | 81.29 | 57.20 | 12.5 |
| 2 | 39.95 | 27.75 | 12.3 |
|  | 40.30 | 27.05 | 11.9 |
| 3 | 39.28 | 27.70 | 12.5 |
|  | 80.50 | 55.60 | 12.2 |
| 4 | 39.25 | 26.75 | 12.1 |
|  | 94.08 | 65.30 | 12.3 |
| 5 | 77.55 | 53.90 | 12.3 |
|  | 61.72 | 43.20 | 12.4 |
| 7 | 45.32 | 31.25 | 12.2 |
|  | 49.26 | 33.75 | 12.1 |
| 10 | 50.71 | 34.20 | 11.9 |
|  | 46.87 | 31.15 | 11.8 |
| 14 | 40.44 | 27.55 | 12.1 |
|  | 38.32 | 25.54 | 11.8 |
| 21 | 66.61 | 45.00 | 12.0 |
|  | 68.78 | 47.00 | 12.1 |
| 28 | 40.16 | 26.10 | 11.5 |
|  | 46.41 | 30.40 | 11.6 |
| 35 | 57.21 | 38.05 | 11.8 |
|  | 51.65 | 33.95 | 11.6 |
| 51 | 25.50 | 13.70 | 9.5 |

$^a$Weight of sample analyzed.
$^b$Volume of 10$^{-2}$N sodium thiosulfate required to titrate the sample at time (T).
$^c$Percentage of positive chlorine in the sample analyzed.

TABLE 6
STABILITY OF 3-CHLORO-2,2-[SPIRO-1'-METHYL-4' PIPERIDINIUM 1,3-OXAZOLIDINE METHANESULFONATE IN THE NEAT STATE AT 40° C

| Time (days) | Wt. (mg)$^a$ | V$_T$(ml)$^b$ | %Cl$^c$ |
|---|---|---|---|
| 0 | 74.29 | 44.35 | 10.6 |
|  | 58.10 | 34.70 | 10.6 |
| 1 | 36.27 | 21.00 | 10.2 |
|  | 60.50 | 35.10 | 10.3 |
| 2 | 34.77 | 20.15 | 10.3 |
|  | 74.49 | 41.45 | 9.8 |
| 3 | 155.01 | 85.95 | 9.8 |
|  | 21.46 | 12.10 | 10.0 |
| 4 | 119.17 | 63.35 | 9.4 |
| 5 | 117.89 | 64.35 | 9.7 |
|  | 72.92 | 39.90 | 9.7 |
| 7 | 37.76 | 19.85 | 9.3 |
|  | 159.15 | 86.80 | 9.7 |
| 10 | 146.99 | 81.70 | 9.8 |
| 14 | 109.44 | 54.65 | 8.8 |
|  | 43.93 | 22.40 | 9.0 |
| 21 | 138.91 | 73.90 | 9.4 |
| 28 | 42.54 | 22.65 | 9.4 |
|  | 69.21 | 35.60 | 9.1 |
| 35 | 114.65 | 57.70 | 8.9 |
|  | 47.36 | 24.05 | 9.0 |
| 51 | 46.23 | 20.80 | 8.0 |

$^a$Weight of sample analyzed.
$^b$Volume of 10$^{-2}$N sodium thiosulfate required to titrate the sample at time (T).
$^c$Percentage of positive chlorine in the sample analyzed.

ANTIBACTERIAL ACTIVITY STUDIES

The procedure employed to determine the antibacterial activity of 3-chloro-2,2,4,4-tetramethyl-tetrahydro-1,3-oxazolidine and 3-chloro-2,2-[spiro-1'-methyl-4'-piperidinyl]-4,4-dimethyl-1,3-oxazolidine was based primarily on a modification of the serial dilution method of analysis. However, instead of determining the minimum inhibitory concentration parameters for the compound investigated, applicants alternatively chose to determine the bactericidal end-point for a given concentration of the compound investigated. Consequently, applicants' studies were established to determine the time required for complete sterilization of the microorganism tested, when exposed to a given concentration of the compound investigated.

The method and reagents employed in applicants' antibacterial studies are described below:

| Organism | ATCC Code | Overnight Broth Culture(Organisms/ml) |
|---|---|---|
| Staph. epidermidis | 12228 | 5 × 10$^6$ |
| E. coli | 10536 | 10 × 10$^6$ |
| Kleb. pneumoniae | 10031 | 12 × 10$^6$ – 13 × 10$^6$ |
| Pseud. aeruginosa | 9027 | 12 × 10$^6$ – 13 × 10$^6$ |
| Staph. aureus | 6538 | 6 × 10$^6$ – 8 × 10$^6$ |
| Bord. bronchiseptica | 4617 | 3 × 10$^6$ |

Nutrient Broth B.B.L. — 8 g/1000 ml distilled water. The broth contains 5 g gelysate peptone and 3 g beef extract. The solution has a pH of 6.9. Nutrient Agar — 23 g/1000 ml. distilled water. The nutrient contains 5 g gelysate peptone, 3 g beef extract and 15 g agar.

Horse Serum T.C. — 10% horse serum solution in distilled water. The serum solution was freshly prepared and adjusted to a pH of 7 using carbon dioxide prior to its use.

METHOD

A stock solution of each compound identified above was prepared using an appropriate buffered solution.

For screening in the absence of a denaturing agent (e.g., horse serum) an equal volume of distilled water and the resulting solution was subjected to the screen.

For screening in the presence of a denaturing agent, a volume of the stock solution was diluted using an equal volume of 10% horse serum. When necessary, the final solution was adjusted to the desired pH using 1N HCl and the solution was permitted to stand at room temperature for thirty minutes prior to the screening procedure.

To 5 ml of the stock solution being evaluated, there was added 0.2 ml of an overnight broth culture containing the particular micro-organism being investigated (see above). At time intervals of 0.5, 1, 2, 3, 4, 5, . . . minutes, a loop of this suspension was subcultured into 5 ml of a sterile nutrient broth. All the samples were then incubated at 37° C for seven days with daily observation for evidence of bacterial growth. The time interval reported is for that sample in which no bacterial growth was observed after the incubation period.

Aside from the foregoing, several controls were also employed as described below.

CONTROL 1

This control was designed basically to insure viability of the overnight broth culture.

To 5 ml of a sterile 0.9% sodium chloride solution, there was added 0.2 ml of an overnight broth culture containing the particular micro-organism being investigated. A loop of this suspension was subcultured into 5 ml of a sterile nutrient broth and incubated at 37° C for seven days.

CONTROL 2

This control was designed to insure that the diution factor of the nutrient broth was beyond any bacteriostatic activity of each compound (as identified above) tested.

To 5 ml of a sterile nutrient broth there was added a loop of a solution of each compound as described above and the solution was mixed immediately. To this soluton, there was then added a loop of an overnight broth culture which was diluted 25× with a 0.9% sodium chloride solution. Incubation was carried out for 7 days at a temperature of 37° C.

CONTROL 3

This control was employed to insure the bacterial growth observed was that due to the organism being tested, rather than contanimation from a foreign organism.

At the same time intervals used for subculturing the test solution into nutrient broth during the screening procedure, a loop of the test solution was also subcultured onto sterile nutrient agar plates. This technique was useful for observing the characteristic colonial morphology of each organism.

CONTROL 4

This control was used initially to insure that the pH of the solution and the concentration of the buffer species did not inhibit the bacterial growth during the time intervals used in the screening procedure.

The entire screening procedure was conducted for each buffered solution using the buffered solution rather than the solution of each tested compound in the procedure.

By following the reaction scheme as illustrated in Examples I and II, all the compounds of the present invention can be prepared.

While all compounds encompassed within applicants' generic formula do meet applicants' criteria, i.e., exhibit sufficient antibacterial and antifungal activity with low chlorine potential and remain non-persistant, still, certain compounds are preferred. These compounds are:

1. 3-chloro-2,2,4,4-tetramethyl-tetrahydro-1,3-oxazolidine,
2. 3-chloro-2,2,4,4-tetramethyl-tetrahydro-1,3-oxazine,
3. 3-chloro-2-methyl-2-(1-diethylamino-3-propyl)-4,4-dimethyl-1,3-oxazolidine or its HX salt,
4. 3-chloro-2-methyl-2-(1-diethylamino-3-propyl)-4,4-dimethyl-tetrahydro-1,3-oxazine or its HX salt,
5. 3-chloro-2,2[spiro-1'-methyl-4'-piperidinyl]-4,4-dimethyl-1,3-oxazolidine or its HX salt,
6. 3-chloro-2-methyl-2-(diethylaminoethyl)-4,4-dimethyl-1,3-oxazolidine or its HX salts,
7. 3-chloro-2-methyl-2-(Diethylaminomethyl)-4,4-dimethyl-1,3-oxazolidine or its HX salts These compounds are conveniently used in aqueous solution. They may be applied by any conventional means, e.g., spray, wipe, etc.

Although the present invention has been adequately described in the foregoing specification and examples included therein, it is obviously apparent that various changes and/or modifications can be made thereto without departing from the spirit and scope thereof.

What we claim is:

1. A method for inhibiting bacterial growth which comprises treating said bacterial growth with an antibacterially effective amount of a compound of the formula:

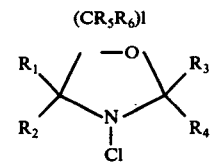

wherein each of $R_1$ and $R_2$ which may be the same of different represents an alkyl group of from 1 to 20 carbon atoms; wherein each of $R_5$ and $R_6$ which may be the same or different, represents a hydrogen atom or alkyl of from 1 to 20 carbon atoms; and wherein each of $R_3$ and $R_4$ which may be the same or different represent

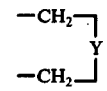

wherein Y represents $-(CH_2)_n-W-(CH_2)_m-$ or $>CH-Z$, wherein W represents a member selected from the group consisting of $-O-$, $-CH_2-$, $>NCH_3$, $>NHCH_3^+$, $>NC_2H_5$, $>NHC_2H_5^+$, $>N(CH_3)_2^+$, and $>N(C_2H_5)_2^+$, wherein $n$ is the same of different from $m$ and wherein each of $n$ and $m$ represent an integer of from 0 to 2 and wherein Z represents a member selected from the group consisting of dimethylamino, diethylamino, trimethylammonium, triethylammonium, dimethylammonium, diethylammonium, $-COOR_7$, $-OOCR_8$ and $-OR_9$, wherein each of $R_7$ through $R_9$ respectively, represent a member selected from the group consisting of alkyl of from 1 to 5 carbon atoms and benzyl; and wherein $l$ represents an integer of 1 or 2.

2. The method of claim 1, wherein $R_1$ and $R_2$ represent an alkyl group of from 1 to 5 carbon atoms.
3. The method of claim 1, wherein $R_5$ and $R_6$ represent an alkyl group of from 1 to 5 carbon atoms.
4. The method of claim 1, wherein $R_5$ and $R_6$ represent a hydrogen atom.
5. The method of claim 1, wherein said compound is: 3-Chloro-2,2-[spiro-1'-methyl-4'-piperidinyl]-4,4-dimethyl-1,3-oxazolidine and its HX salt, wheren X represents a pharmaceutically acceptable anion.

* * * * *